United States Patent
Coleman

(10) Patent No.: US 8,304,602 B2
(45) Date of Patent: Nov. 6, 2012

(54) METHODS FOR MODULATING APICAL BUD DEVELOPMENT IN A PLANT

(75) Inventor: Gary Dale Coleman, Odenton, MD (US)

(73) Assignee: University of Maryland, College Park, MD (US)

( * ) Notice: Subject to any disclaimer, the term of this patent is extended or adjusted under 35 U.S.C. 154(b) by 487 days.

(21) Appl. No.: 11/942,953

(22) Filed: Nov. 20, 2007

(65) Prior Publication Data

US 2008/0178349 A1 Jul. 24, 2008

Related U.S. Application Data

(60) Provisional application No. 60/860,552, filed on Nov. 22, 2006.

(51) Int. Cl.
*C12N 15/82* (2006.01)
*A01H 5/00* (2006.01)

(52) U.S. Cl. ......... 800/278; 800/290; 800/287; 800/298

(58) Field of Classification Search ........................ None
See application file for complete search history.

(56) References Cited

OTHER PUBLICATIONS

Abe et al (2005, Science 309:1052-1056).*
Bowie et al, Science 247:1306-1310, 1990.*
McConnell et al, Nature 411 (6838):709-713, 2001.*
Wigge et al (2005, Science 309:1056-1059).*
Böhlenius, Henrik et al., "CO/FT Regulatory Module Controls Timing of Flowering and Seasonal Growth Cessation in Trees," Science, 312: 1040-1043 (2006).
Rohde, Antje et al., "PtABI3 Impinges on the Growth and Differentiation of Embryonic Leaves during Bud Set in Poplar," The Plant Cell, 14: 1885-1901 (2002).

* cited by examiner

*Primary Examiner* — Stuart F. Baum
(74) *Attorney, Agent, or Firm* — Darlene A. Vanstone, Esq.; Carolyn S. Elmore, Esq.; Elmore Patent Law Group, P.C.

(57) ABSTRACT

The present invention provides methods for regulating the development of apical bud formation in a plant comprising the step of modulating the expression of PtFD1 or a protein having substantial identity to PtFD1, in the plant. Transgenic poplar trees that either overexpress PtFD1 or that down regulate PtFD1 are also provided. Also provided are methods for identifying the regulatory targets of PtFD1.

10 Claims, 2 Drawing Sheets

METHODS FOR MODULATING APICAL BUD DEVELOPMENT IN A PLANT

RELATED APPLICATION

This application claims the benefit of U.S. Provisional Application No. 60/860,552, filed on Nov. 22, 2006. The entire teachings of the above application are incorporated herein by reference.

BACKGROUND OF THE INVENTION

One of the key traits that distinguish temperate annual plants from perennial plants is developmental arrest resulting from vegetative and floral bud dormancy. This single trait is an essential developmental event crucial to the survival of perennial plants during periods unfavorable for growth, such as those encountered during winter. Bud dormancy induction and release is an important developmental problem and little is known about the genes and mechanisms that regulate this developmental process. A prerequisite to bud dormancy is the initiation and development of a bud. Studying bud development and dormancy provides a unique opportunity to unravel genetic and epigenetic factors and mechanisms for both plant and animal adaptation. Besides advancing our understanding of basic tree biology, knowledge of the genetic basis of bud dormancy may uncover novel regulatory mechanisms that will contribute to our general understanding of biology.

Trees are a major part of the terrestrial ecosystems yet research in the basic biology of tree growth and development has lagged behind that of herbaceous plants largely due to the challenges associated with conducting research in trees. Research of certain traits important to tree growth and development can not be performed with annual plants such as *Arabidopsis*, rice or maize for the simple reason that these model annual plant species lack these developmental processes. Bud dormancy is such a trait. Because of the fundamental importance of bud dormancy to adaptation, it has been studied for decades, yet we still lack an understanding of the underlying genetic and molecular mechanisms regulating vegetative bud development, dormancy and dormancy release.

Recently, the forest tree species *Populus* (poplar and cottonwoods) has been successfully used as a model for tree biology. The availability of a tree model in combination with the state of the art in molecular biology, genetic engineering and a variety of other disciplines have now made possible the scientific breakthroughs responsible for the present invention.

SUMMARY OF THE INVENTION

The present invention provides methods for regulating the development of apical bud formation in a plant comprising the step of modulating the expression of PtFD1 or a protein having substantial identity to PtFD1, in the plant. Transgenic poplar trees that either overexpress PtFD1 or that down regulate PtFD1 are also provided. Also provided are methods for identifying the regulatory targets of PtFD1.

DETAILED DESCRIPTION OF THE INVENTION

Figure 1:
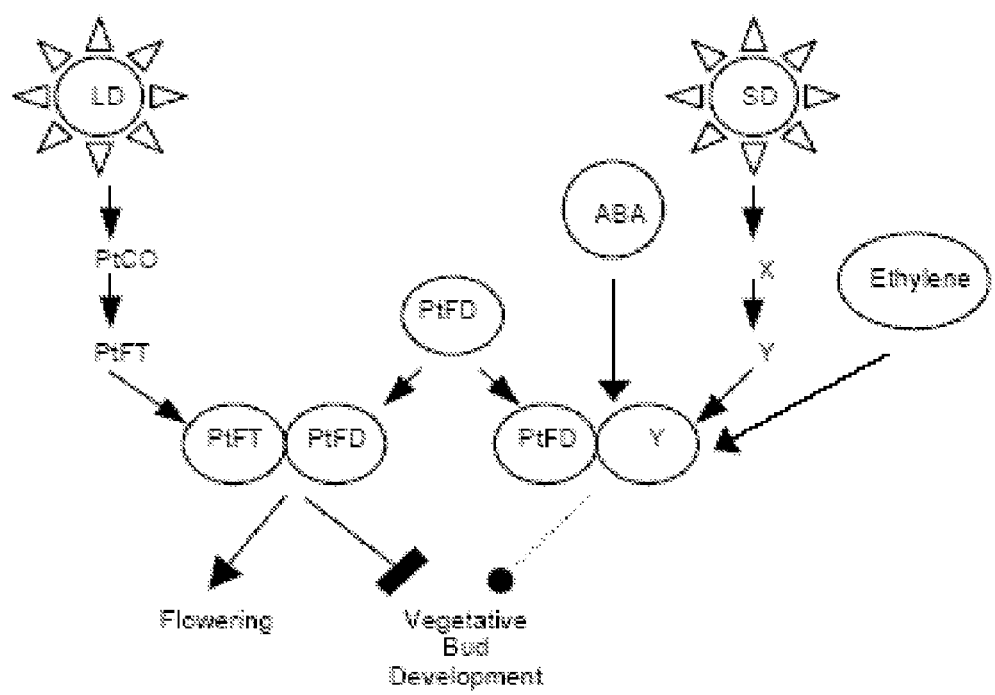
FIG. 1 is a model of photoperiod regulation of poplar flowering and vegetative bud development in accordance with the invention.

A growing body of evidence suggests that vegetative bud development and dormancy involves genetic regulatory circuitry that is analogous to that controlling flowering and to components of the abscisic acid (ABA) signaling pathway. In *Arabidopsis thaliana*, flowering is regulated by multiple genetic pathways that include the autonomous, the photoperiod, the gibberellin and the vernalization pathways. These genetic pathways are integrated by a number of genes including FD, FE, FWA, PDF2, SOCI and FT. Signal integration results in the activation of floral meristem identity genes including LFY and AP1. The photoperiod pathway involves the positive regulation of CONSTANS that activates FT expression in leaves. FT mRNA then appears to somehow be transported to shoot apex where FT then interacts with FD to activate the expression of floral identity genes such as AP1. It is possible that FT may be the long searched for systemic flowering signal "florigen".

The vernalization pathway involves cold temperature (vernalization)-mediated initiation and maintenance of repressive chromatin in the *Arabidopsis* Flowering Locus C (FLC), a MADS box transcription factor and a repressor of flowering. The initiation of repressed FLC chromatin requires VERNALIZATION INSENSITIVE3 (VIN3), a PHD-domain-containing protein that is induced only after a prolonged period of cold. The repressed state of FLC is mitotically stable. This memory (or maintenance) of the repressed FLC chromatin requires the activities of VRN1, a Myb-related DNA-binding protein and VRN2, a homologue of one of the Polycomb group proteins, which maintain the silencing of genes during animal development.

If the theory that analogous regulatory pathways to flowering regulate vegetative bud development and dormancy is correct, then it would be expected that genes related to those in the flowering pathway would be expressed during vegetative bud development and dormancy. In fact, this appears to be the case and recent research with the forest tree species poplar indicates that the CO/FT complex mediates the photoperiod output involved in growth cessation and bud set as well as flowering (Bohlenius et al. (2006) *Science* 312, 1040-1043).

Interestingly, the CO/FT regulation of flowering in poplar appears to be associated with LD photoperiods and a diurnal peak of PtFT1 expression at the beginning of the night (Bohlenius et al. 2006). In contrast, during SD photoperiod associated growth cessation and bud set, PtFT1 expression was suppressed and lacks any diurnal variation (Bohlenius et al. 2006). Furthermore, downregulating PtFT1 expression by RNAi enhanced the sensitivity of these plants to SD (Böhlenius et al. 2006). The present research with the poplar gene similar to the *Arabidopsis* floral integrator FD (PtFD1; previously termed PTBF1; GenBank Accession number AF288616) which demonstrates an important role for PtFD1 in vegetative bud development provides additional support for this theory. It is possible that PtFD1 plays an analogous role to FD in *Arabidopsis* by integrating the spatial specificity of environmental signals. In addition to similarities to flowering pathways, it is also known that the poplar ortholog to ABI3, PtABI3, plays a role in poplar vegetative bud development (Rohde et al. (2002) *Poplar. Plant Cell.* 14, 1885-1901). In *Arabidopsis*, ABI3 is a component of the ABA response pathway involved in processes associated with seed maturation. Although ABA has recently been linked to the autonomous flowering pathway via the ABA receptor FCA, it appears that FCA and ABI proteins are involved in different ABA responses. Whether vegetative bud development pathways analogous to flowering and ABA signaling are distinct or converge at some point to control bud development and dormancy is unknown.

Beyond the molecular similarities between flowering and vegetative bud development and dormancy, morphological similarities between flowering and bud dormancy also exist. Vegetative buds and flowers develop parallel organs with bud scales (cataphylls) being equivalent to sepals and bud stipules being equivalent to petals. Furthermore, flowering and bud dormancy are both subject to regulation by similar environmental factors including photoperiod and chilling.

Without being limited to any one scientific theory, the inventors have developed a crude model based on a functional divergence of PtFD1 (FIG. 1). In this model, during LD photoperiods shoot growth cessation and vegetative bud development is somehow suppressed through the expression of PtFT and a possible interaction with PtFD1 (and possibly PtFD2). This LD interaction results in the induction of flowering. In SD photoperiods PtFD1 expression is enhanced while PtFT1 expression is suppressed and PtFD1 interacts with an unknown factor to modulate vegetative bud development processes as opposed to LD flower induction. The output from the SD PtFD1 module then acts as a negative inhibitor of bud development which might be required to slow development so that developmental and physiological processes are temporally and spatially integrated. Other factors including ABA and ethylene pathways may also be integrated by SD-induced PtFD1, although this is still not known.

Figure 2:
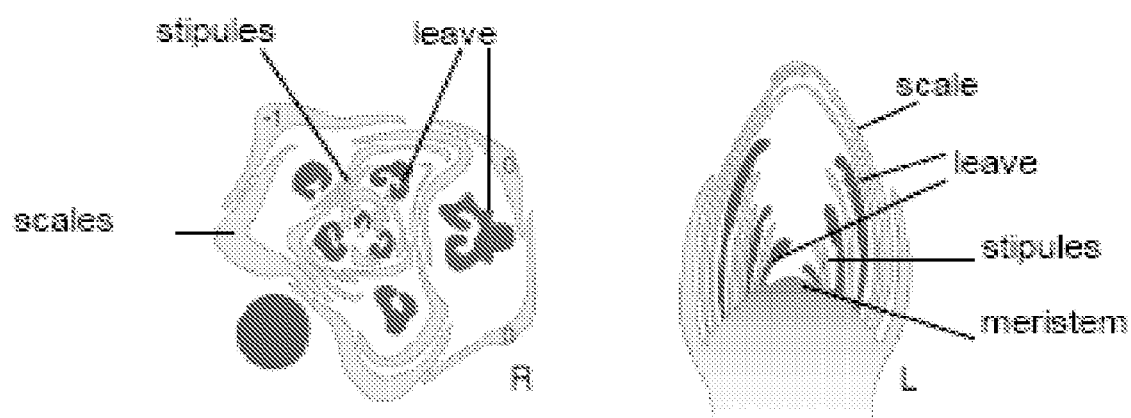
FIG. 2 is a sketch of the poplar apical vegetative bud structure.

Dormancy is an adaptive trait allowing survival of plant structures during unfavorable conditions and broadly defined as the temporary suspension of visible growth or development. Prerequisite to bud dormancy is the formation of an apical bud. Although this seems straightforward, it is a critical aspect of bud dormancy in perennial plants and highlights the importance of bud initiation and morphogenesis to bud dormancy. Poplar exposure to short day (SD) photoperiods (8 hours light/16 hours darkness at 20-25° C.) induces vegetative bud development and dormancy. Apical vegetative buds of *Populus* consist of the shoot meristem, embryonic leaves, and stipules enclosed by two or more pairs of bud scales (FIG. 2). Prior to SD, lateral primordia develop into leaves that are subtended by a stipule. After exposure to SD, the development of lateral primordia is altered and leaf development is either aborted or suppressed while the stipules develop into bud scales (Rohde et al. 2002). Thus, vegetative bud development is an intriguing developmental phenomenon where SD somehow triggers a process that essentially suppresses leaf development while the stipules that subtend these suppressed leaves develop and grow into bud scales.

Many studies have examined a regulatory role for gibberellins (GAs) and abscisic acid (ABA) in tree bud development and dormancy. There is compelling evidence indicating that GAs have a role in SD mediated shoot growth cessation since SD alterations in GA metabolism and SD induced reduction of GA levels are followed by a decline in subapical cell divisions. This SD growth cessation is reversed with exogenous GA1 or with LDs. In contrast, the role of ABA in bud dormancy is less clear. In some cases, ABA levels appear to be correlated with processes associated with bud maturation and freezing tolerance as opposed to photoperiod associated growth cessation and dormancy. Yet, Rohde et al. (2002) observed transient increases in ABA levels in developing apical buds of poplar after 24 to 27 days of SD treatment but failed to observe ABA inducible expression of PtABI3. From this it was speculated that PtABI3 might interact with ABA as opposed to being a component of ABA signal transduction (Rohde et al. 2002). Until recently, ethylene was not considered to have a major regulatory role in tree bud dormancy. However, it has been shown that SD-induced apical bud development was abolished and endodormancy was delayed in transgenic ethylene-insensitive birches. This absence of SD-induced apical bud development and delayed endodormancy was accompanied by a lack of ABA accumulation in the apices of the ethylene-insensitive birches. Its known that ABA and ethylene interact is some processes and bud dormancy may be one of these processes.

Quantitative genetic studies of bud set and spring bud flush have established that these traits are under the control of multiple genes. A QTL mapping study using a mapping pedigree of poplar identified 3 QTLs controlling bud set and 6 QTLs for bud flush. This same study also mapped 5 candidate genes including phytochrome genes (PHYB1 and PHYB2) and genes associated with ABA responses (ABIB, ABI1D and ABI3I) to the QTL map. Interestingly, PHYB2 and ABIB were coincident with QTLs associated with bud set and bud flush, further supporting the importance of photoperiod and potential role of ABA signaling in tree bud development.

Recent studies aimed at the molecular genetics of poplar bud development and dormancy have focused on the poplar ABI3 ortholog (PtABI3) (Rohde et al., 2002), the floral promoter PtFT1 (Bohlenius et al. 2006) and the present research with PtFD by the present inventors as described herein. All three of these genes have roles in poplar vegetative bud development. PtFT1 is part of the CO/FT regulatory system that controls LD flowering in poplar as well as suppressing short day (SD)-induced growth cessation and bud set.

PtABI3 is an ortholog to the *Arabidopsis* B3 domain family of transcriptional regulators involved in ABA-mediated seed maturation although it has been suggested ABI3 may have functions beyond ABA signaling. PtABI3 is an essential component of bud formation and is required for both growth and differentiation of embryonic leaves prior to growth arrest and may direct aspects of cellular maturation (Rohde et al. 2002).

PtFD1, formerly termed PTBF1 (GenBank Accession number AF288616) and now renamed PtFD1, is similar to two *Arabidopsis* bZIP proteins, AtbZIP14 (At4g35900) and AtbZIP27 (At2g17770). *Arabidopsis* At4g35900 encodes the bZIP protein FD that partners with FT in the promotion of flowering. PtFD1 also appears to function as a FD ortholog since overexpression of PtFD1 results in flowering of juvenile poplars grown in long day (LD) conditions (16 hrs light/8 hrs dark at 20-25° C.). Similar to both PtABI3 and PtFT1, altering expression of poplar PtFD1 affects normal bud differentiation and development (see Examples for details).

Given that PtFD1, PtFT1 and PtABI3 have roles in genetic regulatory system that controls the initiation, differentiation and development of vegetative buds in trees raises exciting possibilities of how these genes may accomplish this task. It appears that PtFT1 is the output of the photoperiod environmental signal in a manner similar to the role of FT in integrating photoperiod and the timing of flowering in *Arabidopsis*. Genetic studies in *Arabidopsis* suggest that ABI3 and ABI5 may participate in a common pathway with ABI5 acting downstream of ABI3 (Lopez-Molina et al. 2002). In addition, interactions between ABI5 (or TRAB1, the rice ABI5 homolog) with ABI3 (or VP1) have been demonstrated. Although PtFD1 is most closely related to *Arabidopsis* FD, it is a member of the Group A bZIPs that includes ABI5. From this it is an intriguing suggestion that since PtFD1 expression is both SD- and ABA-inducible as shown herein, that ABA and photoperiod pathways involved in bud development and dormancy may converge and PtFD1 could be a factor that spatially integrates these two pathways. This provides an exciting opportunity to link photoperiod, ABA signaling and vegetative bud development through a genetic regulatory system that uses analogous genetic components to ABA signaling and flowering pathways.

In one aspect, the present invention provides a method for modulating apical bud development in a plant comprising the step of regulating the expression of PtFD1 having the amino acid sequence of SEQ ID NO: 1, a protein having an amino acid sequence with substantial identity to that of PtFD1, or a functional portion thereof in the plant. In a preferred embodiment, the method comprises regulating the expression of PtFD1 having the amino acid sequence of SEQ ID NO: 1 in a plant of the species, *Populus*. The term "the FD protein of interest" will be used herein to collectively refer to PtFD1 having the amino acid sequence of SEQ ID NO: 1 and those sequences having substantial identity with PtFD1 or any functional portion thereof. The term "functional portion thereof" is used herein to designate any peptide fragment of PtFD1 that has one or more of the functional properties associated with the full-length PtFD1 protein. In one embodiment, the one or more functional properties relate to apical bud development. In another embodiment, a functional portion of PtFD1 has the ability to modulate apical bud development in a plant.

As used herein, the term "substantial identity" in the context of two nucleic acid or protein sequences, refers to two or more sequences or subsequences that have for example at least about 60%, preferably at least about 70%, more preferably at least about 80%, still more preferably at least about 90%, even more preferably at least about 95%, and most preferably at least about 99% nucleotide or amino acid residue identity, when compared and aligned for maximum correspondence, as measured using one of the following sequence comparison algorithms or by visual inspection. In one embodiment, in the case of a nucleotide sequence, the percent identity exists over a region of the sequences that is at least about 50 nucleotides in length. In another embodiment, the percent identity exists over a region of at least about 100 nucleotides. In yet another embodiment, the percent identity exists over at least about 150 nucleotides. In a further embodiment, the percent identity exists over the entire length of the coding regions.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity and sequence similarity is the BLAST algorithm, which is described in Altschul et al., J. Mol. Biol. 215: 403 410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, $M=5$, $N=-4$, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89: 10915 (1989)).

As used herein the term "modulating apical bud development" includes inducing, enhancing or arresting apical bud development at any point in development. The present inventors have experimentally identified 5 sequential stages of vegetative apical bud development using a number of poplar genotypes. As discussed herein, the 5 developmental stages of bud development are 1) bud initiation, 2) bud maturation, 3) dormancy induction, 4) endodormancy, and 5) chilling/accumulation. The details of these developmental stages are outlined in Table 1.

As used herein the term "regulating the expression of a protein" comprises up-regulating or down-regulating the expression of an FD protein of interest in the plant by any means. In one embodiment, expression of an FD protein of interest is induced by exposing the plant to short day (SD) treatment as described in the Examples below. In another embodiment, expression of an FD protein of interest can also be induced by contacting the plant, preferably the shoot apices or apical buds, with ABA.

In one embodiment, expression of an FD protein of interest can be down regulated by contacting the plant with an oligonucleotide that inhibits the expression of the FD protein of interest. In one embodiment, the oligonucleotide is an antisense oligonucleotide targeted to all or a portion of the gene encoding the FD protein of interest. In another embodiment, the oligonucleotide is an antisense oligonucleotide targeted to all or portion of a nucleic acid having the nucleotide sequence of SEQ ID NO: 2 or a nucleotide sequence with substantial identity to SEQ ID NO:2. One of ordinary skill in the art will appreciate that an antisense oligonucleotide is a non-enzymatic nucleic acid compound that binds to a target nucleic acid by means of RNA-RNA, RNA-DNA or RNA-PNA (protein nucleic acid) interactions and alters the activity of the target nucleic acid (for a review, see Stein and Cheng, 1993 Science 261, 1004 and Woolf et al., U.S. Pat. No. 5,849,902). As used herein, the target nucleic acid is a nucleic acid that encodes an FD protein of interest or a portion of said nucleic acid encoding an FD protein of interest. In one embodiment, the antisense oligonucleotide is complementary to a single contiguous sequence of the target nucleic acid. In other embodiments, the antisense oligonucloetide can form a loop and binds to a target nucleic acid which forms a loop. Thus, an antisense oligonucleotide can be complementary to two (or more) non-contiguous target nucleic acid sequences, or two (or more) non-contiguous sequence portions of an antisense molecule can be complementary to a target sequence, or both. In one embodiment of the invention, the antisense oligonucleotide has a nucleic acid sequence that is complementary to a nucleic acid having substantial identity to the nucleotide sequence of SEQ ID NO:2 or a portion thereof. It is to be understood that an antisense oligonucleotide of the present invention has a sufficient degree of complementarity to the nucleic acid sequence encoding an FD protein of interest or a portion thereof so as to avoid non-specific binding of the antisense compound to non-target nucleic acid sequences under conditions in which specific binding is desired.

In another embodiment, the oligonucleotide is a double-stranded oligonucleotide. Double-stranded oligonucleotides include, for example, short interfering nucleic acid (siNA), short interfering RNA (siRNA), double-stranded RNA (dsRNA), micro-RNA (miRNA), and short hairpin RNA (shRNA) molecules wherein said double-stranded oligonucleotides are capable of mediating RNA interference (RNAi) against an FD protein of interest. In one embodiment, the double-stranded oligonucleotide is a short interfering RNA (siRNA) capable of mediating RNAi against and FD protein of interest and/or inhibiting the expression of the gene encoding the FD protein of interest. In one embodiment, the FD protein of interest has an amino acid sequence having substantial sequence identity to the amino acid sequence of SEQ ID NO:1. In another embodiment, the FD protein of interest has the amino acid sequence of SEQ ID NO:1. In yet another embodiment, the FD protein of interest is encoded by a nucleic acid having substantial identity to a nucleotide sequence of SEQ ID NO:2. In a further embodiment, the FD protein of interest is encoded by a nucleic acid having the nucleotide sequence of SEQ ID NO:2.

In one embodiment, the invention provides a transgenic poplar tree that overexpresses PtFD1. In another embodiment, a PtFD1-overexpressing poplar has been transfected with a vector, wherein the vector comprises a gene encoding PtFD1 or any functional portion thereof operably linked to a promoter. The expression of the gene may be under the control of a constitutive promoter or of an inducible promoter that initiates transcription only when the host cell is exposed to some particular external stimulus. In the case of a plant, the promoter can also be specific to a particular tissue such as the apical bud or shoot apices. In one preferred embodiment, the promoter is the 35S promoter derived from the common plant virus, cauliflower mosaic virus (CaMV).

In one embodiment, the invention provides a transgenic poplar tree that down-regulates the expression of PtFD1. In one preferred embodiment, the PtFD1 transgenic poplars are transfected with a vector comprising an oligonucleotide capable of down-regulating PtFD1. In one embodiment, the oligonucleotide is an antisense oligonucleotide capable of specifically down-regulating the expression of PtFD1. In another embodiment, the oligonucleotide is siRNA capable of inhibiting the expression of PtFD1 by RNAi.

In one aspect the invention provides a modified PtFD1 protein and an oligonucleotide encoding the modified protein. Modifications to PtFD1 include modification of one or more amino acids by substitution, insertion, deletion and/or chemical modification and post-translational modification of PtFD1. In one embodiment, the PtFD1 protein is post-translationally modified (including, for example, glycosylation or acetylation). In a preferred embodiment, the PtFD1 protein has been modified such that it is post-translationally activated to conduct a genome-wide analysis for targets of PtFD1 regulation using DNA microarrays. In one embodiment, the modified PtFD1 protein is derived from *Populus*. In another embodiment, similar modifications can be made to FD proteins of interest from other plant species. The genetic targets for regulation by PtFD1 and other FD proteins of interest may represent genes that regulate or specify processes associated with vegetative bud development. Identification of these genes will significantly advance our understanding of the genetic basis of vegetative bud development in trees.

The methods of the invention are useful in the fields of agriculture and forestry. For example, the methods of the invention may be used to either extend or shorten the duration of tree growth to match the climatic conditions of a specific location. The methods of the invention may also be used to eliminate dormancy of temperate fruit tree species grown in tropical and sub-tropical regions, thereby extending fruit production and harvest.

The invention is further described by the following non-limiting examples.

Example 1

Apical Bud Development in *Populus*

The inventors have experimentally defined 5 sequential stages of vegetative apical bud development using a number of poplar genotypes including *Populus trichocarpa* clone 'Nisqually-1' (genotype used for the genome sequence) and *Populus alba×tremula* clone 717-1B4 (widely used for transgenic studies) (Table 1).

TABLE 1

| | | | Dormancy Stage | | |
|---|---|---|---|---|---|
| | Bud Initiation | Bud Maturation | Dormancy Induction | Endodormancy | Chilling Accumulation |
| Experimental Induction | Weeks 1-3 of SD exposure @ 25° C. | Weeks 3-6 of SD exposure @ 25° C. | Weeks 6-8 of SD exposure @ 25° C. | Weeks 8-12 of SD exposure at 10° C. day/4° C. night | Weeks 12-16 of SD exposure at 10° C. day/4° C. night |
| Features | Reduced stem elongation -Bud scale initiation and growth -Enclosure of internal bud structures - | Increased bud DW - Accumulation of storage reserves - Water content declines Shoot growth | Bud growth ceases - Water content reduced -Acquisition of desiccation tolerance Shoot growth | Meristem quiescence -Bud break and shoot growth does not occur in LD (>6 month delay) | Number of days required for bud break and shoot growth to resume in LD declines Bud water |

TABLE 1-continued

| | | Dormancy Stage | | |
|---|---|---|---|---|
| Bud Initiation | Bud Maturation | Dormancy Induction | Endodormancy | Chilling Accumulation |
| Shoot growth resumes in LD | resumes in LD | delayed in LD | | content increases |

Apical bud initiation occurs during the first 3 weeks of SD exposure (8 hrs light/16 hrs darkness at 20-25° C.). Initiated buds differentiate and develop with continued SD exposure (3-6 weeks at 20-25° C.). During these first 2 stages, bud break and shoot growth will readily resume (within 1-2 weeks) if plants are exposed to long day (LD) conditions (16 hrs light/8 hrs dark at 20-25° C. instead of SD. Apical buds begin to enter dormancy after 6 weeks of SD treatment and with continued SD treatment at a lower temperature (10° C. day/4° C. night) the buds become endodormant and require an extended time period (greater than 6 months) to resume growth if switched to LD at 25° C. Once endodormant, low temperatures have an opposite effect and chilling accumulation results in the release from endodormancy (weeks 12-16) and apical buds resume growth when exposed to LDs at 25° C. With this experimental regimen we can cycle plants through a complete dormancy cycle in 16 weeks, which facilitates experimental studies of bud development and dormancy.

Example 2

PtFD1 Encodes an Ortholog to the *Arabidopsis* bZIP Transcription Factor FD During a study directed at discovering potential transcription factors expressed during vegetative bud development using degenerate PCR primers, the present inventors cloned the bZIP transcription factor PtFD1 GenBank accession Number AF288616. Sequence analysis reveals that PTFD1 is similar to members of the *Arabidopsis* bZIP Group A (ABI5/ABF/AREB) family of transcription factors with greatest similarity to the bZIP transcription factor FD (AtbZIP14, At4g35900) and AtbZIP27 (At2g17770). Based on TBLASTN searches of the poplar genome using either *Arabidopsis* FD or PtFD1 and phylogenetic analysis with PAUP a second gene related to PtFD1 was identified in the poplar genome (JGI gene model grail3.0003013801) and is referred to as PtFD12. Unlike PtFD1, PtFD12 does not show photoperiod associated changes in expression (detailed below).

Example 3

PtFD1 is Expressed in Developing Apical Buds and is Both SD and ABA Inducible PtFD1 transcript levels increase in shoot apices and developing apical buds within 3 weeks of SD treatment. PtFD1 mRNA levels continue to increase with SD treatment and reach a maximum after 4 to 6 weeks of SD treatment and then decline with continued SD exposure beyond 6 weeks. It is noteworthy that PtFD1 expression is coincident with SD bud differentiation and when SD induced plants are subsequently treated with LD mRNA levels decline. Besides apical buds, PtFD1 expression is also detected in axillary buds, albeit at much lower levels compared to apical buds, and is not detected in leaves or bark (results not shown). In situ hybridization studies reveal that PtFD1 mRNA is found in the shoot, meristem, leaf primordia, embryonic leaves and developing stipules (data not shown). Consequently, the temporal and spatial expression of PtFD1 is concurrent with apical bud differentiation suggesting a role in tree bud development. In addition to SD induction, PtFD1 expression can also be induced in LD grown shoot apices when treated with ABA. Interestingly this is in contrast to the results for PtABI3 where ABA inducibility was not observed (Rohde et al. 2002). Since PtABI3 and PtFD1 are part of a regulatory system governing vegetative bud differentiation, it is intriguing to speculate that PtFD1 could be the ABA inducible component of this system. It should be noted that multiple bands (3) are present in both the Northern blot and RT-PCR analysis. Because the RT-PCR analysis was performed with DNA primers specific to PtFD1 the bands were cloned and sequenced to verify that they corresponded to PtFD1 transcripts. From this it was concluded that they represent that processed transcript of PtFD1 (smaller band), a PtFD1 transcript that retains a single intron (middle band) or both introns (upper band) and not transcripts of PtFD2. Hence, we are confident that the multiple bands are not transcript originating from different genes. We have also examined the expression of PtFD2 and in contrast to PtFD1 expression of the PtFD2 does not change in response to SD.

Example 4

SD-Induced Vegetative Bud Differentiation and Development is Suppressed in Transgenic Poplars Overexpressing PtFD1

The inventors have produced multiple independent lines of transgenic poplars that overexpress PtFD1 using the 35S promoter. In vitro shoot cultures grown in 0.5× strength Murashige and Skoog (MS) medium (Murashige, T., Skoog, F. 1962. Physiologia Plantorum 15:473-497) were used as starting material. Stem sections about 0.5 cm long were cut longitudinally and precultured on MS medium supplemented with 10 uM 1-naphthalene Acetic Acid and 5 uM 2-isopentenyadenine (M1) for 48 hours in the dark. Precondition stem segement were then inoculated with a 2-day old culture of Agrobacterium (Strain C58 pmp90) at an approximate concentration of $5 \times 10^8$ colony forming units/ml (OD 660 nm=0.3). Stem segments were dipped into 25 ml of bacterial suspension in Petri dishes in containing liquid M1 medium supplemented with 50 ug/L kanamycin and 20 ug/L gentamycin. After 16 hours of incubation, inoculated stem sections were blotted dry and placed on solid M1 medium for 48 hours in the dark. After this inoculation, explants were decontaminated by washing with sterile water containing 25 mg/l tetracycline, 500 mg/l carbenicillin, and 250 mg/l cefotaxime. Decontaminated stem sections were then placed on M1 medium supplemented with 500 mg/l carbenicillin, and 250 mg/l cefotaxime for 15 days in the dark. Shoots were regenerated by transferring stem sections to MS medium supplemented with 0.1 uM thidazuron, 500 mg/l carbenicillin, and 250 mg/l cefotaxime and 5 mg/l glufosinate ammonium.

Compared to wild-type control poplars, PtFD1 overexpressing poplars are characterized by reduced internodal elongation, stem diameter and leave size when grown in LD. Furthermore, the leaves of these plants display a curled phenotype. Interestingly, this phenotype is similar to that observed in *Arabidopsis* that overexpress FD (Wigge et al. (2005) *Science* 309,1056-1059) When the PtFD1 overexpressing poplars are placed in SD, vegetative apical bud development does not occur. The failure of these plants to develop an apical bud appears to be a consequence of suppressed bud scale development and reduced stipule and embryonic leaf production and development. This demonstrates the importance of PtFD1 to bud differentiation and development.

Example 5

Flowering is Induced in LD Grown Transgenic Poplars Overexpressing PtFD1

During the production of transgenic poplars that overexpress PtFD1 it was observed that flowers were often induced in the axillary buds of the shoot cultures. Flower induction was also observed for all of the transgenic lines when grown in a LD greenhouse. Furthermore, the flowers induced in the PtFD1 overexpressing poplars resemble normal flowers and arose only in the axillary buds and not the shoot apex. It is noteworthy that flower induction has not been observed in SD grown PtFD1 overexpressing plants. These results are similar to the induction of flowering in juvenile poplars that overexpress PtFT1 (Bohlenius et al. 2006). These results suggest that LD photoperiod-induced flowering in poplar involves a regulatory pathway similar to that in *Arabidopsis*. This requires that PtFD1 expression occur in the apices of LD grown poplars. The data showed that a low level of expression is observed in apices of LD plants. It seems likely that the PtCO/PtFT regulatory module integrates the LD environmental signal that is then spatially integrated in the shoot apex by PtFD1. In *Arabidopsis* the FT/FD complex then appears to activate floral identity genes such as AP1 (Wigge et al. 2005, supra). This also appears to be the case for poplar since the expression of a number of flower-identity genes including AP1-like, AP3/PI-like and SVP-like is either induced or elevated in PtFD1 overexpressing poplars. This also raises the possibility that altered bud development during SD in PtFD1 overexpressing plants may be a consequence of the activation of these or other MADS-box genes that impinge on apical bud differentiation.

Example 6

PTFD1 RNAi Expression Also Impinges on Bud Development

In addition to PtFD1 overexpressing poplars, we have also produced transgenic poplars where PtFD1 expression is down-regulated by RNAi. The transgenic poplars were prepared as described in Example 4.

The down-regulation of PtFD1 by RNAi is specific to PtFD1 and has no effect on the level of PtFD2 transcripts. Unlike overexpression of PtFD1, reducing PtFD1 expression by RNAi does not result in an obvious LD phenotype. However, apical bud formation appears to be accelerated during SD in PtFD1 down-regulated plants. This appears to be a consequence of enhanced bud scale formation. Suppression of either PtFD1 or PtFT influences SD-induced bud development and the PtFT response appears to be related to enhanced sensitivity to SD photoperiods while the PtFD1 response is likely to be a consequence of bud organ differentiation. Such a result is consistent with PtFT being the integrator of environmental signals and PtFD1 integrating the spatial action of PtFT.

Example 7

Identification and Analysis of Genetic Factors That Interact with PtFD1

Introduction: Our research clearly establishes that PtFD1 has a functional role in polar apical bud differentiation and development. Our initial results, in combination with what is known about the importance of PtABI3 and PtFT to poplar bud differentiation, provide a framework for elucidating regulatory genes in vegetative bud development. This will provide a major advance in our understanding of this important developmental process. Based on our research and the current state of knowledge of vegetative bud development in trees, we believe that PtFD1 is part of a regulatory pathway involved in vegetative bud differentiation and integrates environmental signals to spatially modulate the development of embryonic leaves, stipules and bud scales. We propose that this regulatory pathway involves analogous genetic components to flowering and ABA signaling pathways. We propose to identifying factors that interact with PtFD1 and candidate genes regulated by PtFD1; these factors should include genes that are comparable to components of flowering and ABA signaling pathways.

Because FT-FD interactions form an activation complex involved in the photoperiod flowering pathway in *Arabidopsis* we will first determine if PtFD1 and PtFT interact. Because the poplar genome contains 2 PtFT genes, PtFT1 and PtFT2 (Böhlenius et al. 2006, supra) we will also determine if PtFT2 interacts with PtFD1. In addition, potential PtABI3-PtFD1 interactions will also be determined. Since bZIP proteins can form heterodimers, we will also determine if PtFD1 and PtFD2 interact. Finally we will conduct a cDNA library screen from both LD and SD grown plants to identify additional PtFD1 interacting factors.

A. Yeast Two-Hybrid Assays With Specific Proteins

Assays will be performed essentially as described by Sridhar et al. (2004) *Proc Natl Acad Sci USA* 101, 11494-11499). First the full length cDNAs for PtFD1, PtFT1, PtFT2, PtABI3, PtFD2 and PtABI3 will be individually cloned into both pGBKT7 (DNA-binding domain vector) and pGADT7 (activation domain vector) (BD Biosciences Clontech). Assays in which PtFD1 serves as the BD-bait and PtFT1, PtFT2, PtABI3, PtFD2 or PtABI3 serves as the AD-prey will be contransformed into yeast(AH109) and assayed for β-galactosidase activity following the supplier's procedures (BD Biosciences Clontech). We will also conduct reciprocal assays where PtFT1, PtFT2, PtABI3, PtFD2 and PtABI3 are cloned in pGBKT7 (BD-bait) and PtFD1 is cloned in pGADT7 (AD-prey). Although interactions among PtFT1, PtFT2, PtABI3, PtFD2 and PtABI3 are possible, we will not address those in this study since the aim and focus is to identify factors that interact with PtFD1.

B. In Vitro Pulldowns.

To verify any PtFD1 interactions with the various proteins discovered in the yeast two-hybrid assays we will determine if PtFD1 and the specific interacting protein physically interact in vitro by GST affinity chromatography essentially as described by Sridhar et al. (2004). PtFD1 cDNA will be cloned into the pGEX-4T-1 vector (Pharmacia) to generate a GSTPtFD1 fusion. The cDNA for the interacting factor (PtFT1, PtFT2, PtABI3, PtFD2 or PtABI3) will be cloned into pMAL-C2 vector (NEB) to generate a MBP-ABI3 fusion. GST-PtFD1-fusion proteins will be immobilized on the glutathione resin and incubated with MBP-PtFT1, PtFT2, PtABI3, PtFD2 or PtABI3-fusion proteins. After appropriate incubation conditions, washes and sample preparations, the retention of MBP fusion proteins by GST-PtFD1 are analyzed by Western blots using anti-MBP antibody (NEB). The specificity of the interaction will be tested using purified MBP and a MBP-LUFS fusion (Sridhar et al. 2004). If necessary, we will also verify interactions using a split GFP assay that relies upon the transfection of plant protoplasts (we will use *Arabidopsis* and poplar) and the visualization of interactions by bimolecular fluorescence complementation (BiFC) (Walter et al. 2004). The CO-PI is currently optimizing this system in the lab using *Arabidopsis*.

C. Yeast Two-Hybrid cDNA Screen to Identify Other Interacting Factors.

A cDNA library will be constructed from mRNA purified from shoot apices and developing apical buds of *Populus trichocarpa* 'Nisqually-1' grown in either LD or SD. For the SD library mRNA will be pooled from developing apical buds after 3, 4, 5 and 6 weeks of SD since this is when PtFD1 is expressed. The cDNA library will be constructed and screened using the BD Matchmaker Library Construction and Screening kit from BD Biosciences. Protein interactions will be identified by contransformation of yeast (AH109) with a full length cDNA of PtFD1 cloned into pGBKT7 (DNA-binding domain vector) and the cDNA library cloned into pGAdT7-Rec (AD cloning vector) and assaying for β-galactosidase activity following the supplier's procedures (BD Biosciences Clontech). cDNA clones that interact with PtFD1 will be isolated and sequenced and used to search the poplar genome database (http://genomejgipsf.org/Poptr1/Poptr1.home.html) allowing us to identify the various genes. From this we will select candidate genes based on (a) similarity to known genes involved in ABA signaling or flowering pathways, (b) similarity to transcription factors, or (c) similarity to components of other signal transduction pathways, and (d) analysis of expression patterns in developing apical buds. Selected candidate gene interactions with PtFD1 will then be further verified by co-immunoprecipitation using the BD Matchmaker Co-IP system (BD Biosciences Clontech). Briefly, this involves the transcription and translation of epitope-tagged (c-Myc or HA-tag) bait (i.e. PtFD1) and library proteins using 35S-Met. The translation products are mixed, immunoprecipitated with c-Myc monoclonal antibody or HA-Tag polyclonal antibody, resolved by SDS-PAGE followed by phosphorimaging.

D. Results.

Because the Co-PI has successfully used both yeast hybrid assays and pulldown assays to study the interaction of *Arabidopsis* LEUNIG and SEUSS (Sridhar et al., 2004) we do not anticipate any difficulties in the technical aspects of this section. Caution must be used in interpreting the results of these experiments since that assays are based on interaction in yeast or in vitro interactions. These may not represent true poplar in vivo interactions. Confirmation of in vivo interactions will require additional research such as transformation with epitope tagged proteins to verify interactions through immunoprecipitation studies. It's difficult to estimate the number of candidate genes that may be identified. By selecting only those genes based on the above criteria, we hope to obtain a manageable number of genes for further investigation.

Example 8

Identification and Analysis of Genes That are Targets for Regulation By PTFD1

We propose that PtFD1 is a component of a regulatory pathway involved in the differentiation of vegetative apical buds and may act by providing spatial specificity to environmental inputs. This may be accomplished through a PtFD1 complex with interacting factors that then activates genes involved in apical bud differentiation and development. With this in mind, we put forward that it might be possible to identify gene targets for PtFD1 regulation through the genome-wide analysis of gene expression by exploiting transgenic poplars with altered PtFD1 expression. A similar approach has been used during photoperiod-induced flowering in Arabidopsis to identify CO- and FT-dependent targets and LFY dependent targets of floral induction (Schmid et al. (2003) *Development* 130(24), 6001-6012. However, one of the limitations to this approach is that is difficult to determine where the genes fit into the regulatory network and if they are direct as opposed to indirect targets for activation. To overcome this limitation we will use a second approach that relies on the use of a gene fusion of PtFD1 and the hormone-binding domain of the rat glucocorticoid receptor (GR) that will allow for the post-translational activation by treatment with the synthetic steroid hormone dexamethasone. Such an approach was elegantly used to identify LFY target genes in a tissue culture based system. In this approach we will use a transgenic poplar cell culture system that harbors a 35S:PtFD1-GR fusion to conduct a genomewide DNA microarray analysis to identify targets for PtFD1 activation. After identifying these targets we will verify both the activation and expression of PtFD1 targets in both transgenic and wild-type poplars. By comparing the results from the PtFD1 transgenic poplars with the results from the 35S:PtFD-GR study we should be able to segregate genes that are direct targets for PtFD1 from genes that are part of the regulatory network.

A. Genome-Wide Microarray Analysis of PtFD1 Transgenic Poplars.

Shoot apices and differentiating buds will be collected from LD grown plants of each of the three types of poplars (nontransgenic, PtFD1 overexpressing and PtFD1 RNAi) and after 3, 4, 5 and 6 weeks of SD treatment. RNA from the SD treatments will be pooled within each genotype and replication. Apices and buds will be collected at the middle of the LD or SD light cycle. RNA will be extracted with the Plant RNeasy Mini kit (Qiagen). ~5 ug total RNA will be used as starting material to synthesize double stranded cDNA with oligo (dT)-T7 primers. The cDNA will serve as a template for synthesis of biotinylated cRNA using the BioArray High Yield Transcript Labeling kit (Enzo). Biotinylated cRNA will be cleaned with RNeasy columns (Qiagen). 20 ug of concentration-adjusted cRNA will be fragmented and then hybridized to the Affymetrix Poplar chip (described in supplementary materials section) according to the Affymetrix GeneChip protocol. Three independent biological samples per genotype will be used in the analysis. Thus probes from each type of poplar (control, PtFD1 overexpressing or PtFD1 RNAi) and each biological sample will be hybridized to independent DNA microarrays.

B. Genome-Wide Microarray Analysis of Poplar Cell Cultures Transformed With PtFD1-GR.

A PtFD1-GR fusion will first be created that consists of the PtFD1 open reading frame fused to amino acids 508 to 795 of the rat glucocorticoid receptor using standard cloning procedures. This fusion will then be cloned into the pB7WG2

(Karimi et al. (2002) *Science* 7, 193-195) to create p35S::PtFD1-GR. This *Agrobacterium* binary plasmid will then be used to produce transgenic poplar cell cultures. Since *Populus trichocarpa* is difficult to transform, we will use the poplar hybrid *Populus alba×tremula* clone 717-1B4 since the gene sequences among different species of poplar is highly conserved (Ingvarsson (2005) *Genetics* 169, 945-953). Using glufosinate ammonium resistant callus growing from *Agrobacterium* infected stem sections we will produce both transgenic cell suspension cultures as well as regenerate transgenic plants. Since it takes time to regenerate and propagate transgenic poplars, using transgenic cell suspension cultures that can be produced early on in the project followed by verification with regenerated plants provides an efficient use or resources and time Before conducting DNA microarray analysis we will first confirm that PtFD1 is expressed in the transgenic cell suspension cultures using RT-PCR analysis. To identify genes whose expression changes significantly in response to PtFD1-GR activation, transgenic cell suspension cultures will be treated with 5 uM dexamethasone (dex) plus 10 uM cycloheximide (cyc) in 0.1% ethanol or 0.1% ethanol only for 0, 2, 4, 6, 8, 10, 12 or 24 hours. After each of the treatment periods, RNA from the cells suspension cultures will be purified and prepared for DNA microarray analysis as describe previously. Three independent cell suspension lines will be used in the analysis.

C. Data Analysis.

Each experiment (i.e experiment A with PtFD1 transgenic poplars or experiment B with cell cultures transformed with the PtFD1-GR fusion) will be analyzed separately. Triplicate experiments will be performed with independent RNA isolations and independent hybridizations. Assessment of triplicate quality will be based on linear regression statistics of all three pair-wise comparisons. For comparison across different arrays, raw data will be scanned using the global intensity of all probe sets on each array. Signal intensities for each probe set will be estimated from .CEL files using Affymetrix Microarray Suite (MAS) 5.0. Expression values will be imported into GeneSpring 5.1 (Silicon Genetics) and normalized to the 50th percentile of each array for further analysis. Certain genes such as PtFLC, PtSVP, PtFD1, PtBSP, and PtBGLUC, whose expression is known to decrease or increase during bud development, will serve as an internal control for the experiment and it will allow us to determine both the sensitivity and the reliability of the hybridization.

To identify genes in experiment A whose expression changes significantly during LD or SD or from PtFD1 expression, gene expression will be compared between (1) LD grown control and LD PTFD1 overexpressing plants, (2) LD grown PTFD1 RNAi and LD PTFD1 overexpressing plants, (3) SD grown control and SD PTFD1 RNAi plants, (4) SD grown PTFD1 RNAi and SD PTFD1 overexpressing plants, and (5) LD and SD grown control plants. For experiment B gene expression will be compared between hex+cyc treated cells compared to mock treated cells over the treatment intervals. Genes whose expression changes significantly (P-value <0.001) for any of the comparisons in experiment A or time points in experiment B will be identified. Once these genes are identified, genes common to both experiments represent genes that are candidates for regulation by PtFD1. Through a systematic analysis of these pair-wise comparisons we should be able to identify candidate genes involved in this developmental network. Hierarchical analyses may be used to identify groups of genes with related expression patterns. Genes will also be parsed in the context of Gene Ontology classification, and analyzed for the presence of transcription regulators and DNA binding proteins. Data will be categorized in several formats based on hierarchical categories including hierarchical clustering of changes in expression level, and Gene Ontology category.

The expression profile of individual candidate gene selected through the above processes will be experimentally tested. RNA will be isolated from the bud tissues during SD induced bud differentiation and development and serve as the templates for RT-PCR using gene-specific primers. It is expected that candidate genes regulated by PtFD1 should show increased or decreased expression patterns co-incident with PTFD1 expression. In addition, we will also verify expression of candidate genes in poplars transformed with the PtFD1-GR fusion by treating shoot apices of LD grown plants with hex and cyc and then assaying the expression of the candidate genes by RT-PCR. It is difficult to estimate the number of candidate genes we will identify through this process. Based on the results of Wagner et al. (2004) *Plant J.* 39, 273-282, we anticipate that the number of genes will be less than 100.

D. Results.

We expect that a significant number of genes with altered expression during apical bud development will be identified through this analysis. The challenge will be to identify those with the greatest likelihood of being activated by PtFD1. The chances of finding those genes will be greatly enhanced through the use of transgenic poplars with altered PtFD1 expression combined with the cell culture system using PtFD1-GR fusion. Given the challenges of conducting research with trees, we feel that this dual approach provides a powerful method to develop a collection of candidate genes for PtFD1 activation that can serve as a resource for the research community to further investigate vegetative apical bud development.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of modulating apical bud development in a perennial plant comprising regulating the expression of an FD protein of interest in the perennial plant by transformation, wherein the amino acid sequence of said FD protein of interest comprises SEQ ID NO:1 and wherein the regulation of expression of the FD protein of interest modulates bud development in the transformed plant.

2. The method of claim 1 wherein the expression of the FD protein is induced in the plant.

3. The method of claim 2 wherein SEQ ID NO:1 expression is induced by exposing the plant to Short Day (SD) treatment.

4. The method of claim 2 wherein SEQ ID NO:1 expression is induced in the plant by contacting the plant with abscisic acid (ABA).

5. The method of claim 4 wherein the bud of the plant is contacted with ABA.

6. The method of claim 1 wherein the plant is genetically engineered to overexpress the FD protein of interest.

7. The method of claim 6 wherein the plant is transfected with a vector comprising a promoter operably linked to the gene expressing the FD protein of interest.

8. The method of claim 7 wherein the vector comprises the 35S promoter operably linked to SEQ ID NO:1.

9. The method of claim 1 wherein the plant is of the *Populus* species.

10. A transgenic poplar that overexpresses SEQ ID NO:1 and wherein the overexpression modulates bud development in the plant as compared to a plant not overexpressing SEQ ID NO:1.

* * * * *

SEQUENCE LISTING

<160> NUMBER OF SEQ ID NOS: 2

<210> SEQ ID NO 1
<211> LENGTH: 301

<212> TYPE: PRT
<213> ORGANISM: Artificial Sequence
<220> FEATURE:
<223> OTHER INFORMATION: Synthetic

<400> SEQUENCE: 1

Met Trp Ser Ser Pro Gly Ala Asn Ile Asp Asn Asn Thr Ser Asn
1               5                   10                  15

Ser Lys Val Ser Gly Asn Ser Pro Ser Lys Cys Phe Ser Ser Thr Cys
            20                  25                  30

Ser Ser Pro Ser Pro Pro Ser Pro Ser Pro Pro Ile Pro Asn Gln Ser
            35                  40                  45

Met Asn Gly Ala Ser Met Glu Glu Val Trp Asp Asp Ile Asn Leu Ala
    50                  55                  60

Ser Leu His Asp His Ser Asn Thr Asn Thr Ser Ser Asn Thr Asn His
65                  70                  75                  80

His Ser Phe Asn Gly Met Val Phe Gln Asp Phe Leu Ala Arg Pro Ser
                85                  90                  95

Asn Lys Asp Thr Ser Thr Arg Ala Ala Ser Lys Glu Pro Ser Ser Gly
            100                 105                 110

Gly Gly Asn Ser Phe Leu Lys Asn Ser Leu Gly Pro Pro Pro Ala Thr
            115                 120                 125

Met Leu Ser Leu Asn Ser Gly Ser Asp His Phe His Tyr Leu Glu Ser
130                 135                 140

Ser Asn Thr Val Pro Val Arg Pro Asn Pro Gln Met His Ser His Ala
145                 150                 155                 160

Asn Gly Gly Thr Ile Ser Phe Asp Ser Ser Leu Asp Ser Pro Phe Asp
                165                 170                 175

Ala Leu Gly Ser Ser Ser Ala Phe Leu Ser Ile Cys Lys Lys Arg Pro
            180                 185                 190

Gln Glu Asn Gly Asp Val Ser Gly Gly Asp Arg Arg His Lys Arg Met
            195                 200                 205

Ile Lys Asn Arg Glu Ser Ala Ala Arg Ser Arg Ala Arg Lys Gln Glu
    210                 215                 220

Ser Ser Ser Pro Phe Glu Asn Leu Phe Leu Val Lys Phe Asn Asp Tyr
225                 230                 235                 240

Arg Met Leu Met Phe Tyr Leu Leu Leu Ile Leu Gln Ala Tyr Thr Val
                245                 250                 255

Glu Leu Glu Arg Glu Ala Ala His Leu Ala Gln Glu Asn Ala Lys Leu
            260                 265                 270

Arg Arg Gln Gln Glu Arg Phe Leu Ala Ala Pro Ala Gln Leu Pro
            275                 280                 285

Lys Lys Asn Thr Leu Tyr Arg Thr Ser Thr Ala Pro Phe
    290                 295                 300

<210> SEQ ID NO 2
<211> LENGTH: 1466
<212> TYPE: DNA
<213> ORGANISM: Artificial Sequence
<220> FEATURE:
<223> OTHER INFORMATION: Synthetic

<400> SEQUENCE: 2
gaagtcaatc agaaagaaac atcatttcat ctccagttac tcctagtgct gttttccctg     60
tcaaagcatg tggtcatcgc caggagcaaa tattgataac aacaacacga gcaacagtaa    120
agtctctggc aattctcctt caaaatgctt ttcctctaca tgttcttctc cttcacctcc    180

-continued

```
ctctccttct cctccaatac caaaccaatc aatgaacgga gcctcaatgg aagaagtttg      240
ggatgacata aacctagctt ctcttcatga tcattcaaat actaacacaa gcagcaacac      300
caaccaccat tcttttaatg gtatggtctt tcaagatttc ttggctagac cttccaataa      360
agacacatca acaagggctg cctctaagga accctcctct ggcggggggca acagtttctt      420 gaagaactct ttagggccac ccccagctac catgctgagt ttgaattctg ggtctgatca      480
ttttcattat ctggaaagca gtaatactgt ccctgtgagg ccaaatccac aaatgcatag      540
tcatgccaat ggtggcacaa taagttttga ttcttctctc gattcccct tcgatgcctt       600 gggttcttct tcagcgttcc tttccatttg caaaaaaagg cctcaagaaa acggtgatgt      660
ctctggcggc gatcggaggc acaagcgcat gatcaagaac agagaatctg cagctcggtc      720
ccgggctaga aagcaggaat ctagctctcc ttttgaaaat ttgttttttag tgaaatttaa     780 tgattataga atgttaatgt tttatctttt actaattttg caggcttaca cagttgagtt      840
ggaacgtgaa gctgctcatt tagcacaaga gaatgccaag cttagaaggc agcaagaaag      900
gttcttggca gcagctcctg ctcagctacc aaaaaaaaac accctctata gaacctcaac      960
agctccattt tgagaataca ttaatcccac ttgctctttt cacccatctt tctggcttcc     1020
caaatttatc cttaaaggag agtgagatgt ttccaatgta atattgcaat ggcttttgct     1080
gttgtgttag atacatctca atcaagcggc tgtggtgaca ggaggacaaa caaaagctag     1140
gaaagtggta aggacaaaat aaagttgcat ggattggaag ccgcaggacc agtggagggt     1200
tcttattttt gtttgcttta actattcctc gactctcttg tcttctttcc catttctgct     1260
tttatgcttc ttcccactaa agacgctggg atgttgggac agataaatgc gagtgaaata     1320
gcattttcta gtcttttttgc ctgtaaatat gcatctccgt ttggctacca aaaaaaaaaa     1380
aaaaaaaaaa aaaaattttc tagtctttt gcctgtaaat atgcatctcc gtttggctac     1440
caaaaaaaaa aaaaaaaaaa aaaaaa                                          1466
```